(12) United States Patent
Oh et al.

(10) Patent No.: US 8,206,309 B2
(45) Date of Patent: Jun. 26, 2012

(54) BLOOD PRESSURE MONITORING APPARATUS AND METHOD

(75) Inventors: Hyun Ho Oh, Seoul (KR); Bong Chu Shim, Seoul (KR); Youn Jae Lee, Seoul (KR); Kwy Ro Lee, Seoul (KR); Seong Moon Cho, Seoul (KR); Hyung Ki Hong, Seoul (KR)

(73) Assignee: LG Electronics Inc., Seoul (KR)

( * ) Notice: Subject to any disclaimer, the term of this patent is extended or adjusted under 35 U.S.C. 154(b) by 1118 days.

(21) Appl. No.: 12/062,838

(22) Filed: Apr. 4, 2008

(65) Prior Publication Data

US 2008/0249382 A1    Oct. 9, 2008

(30) Foreign Application Priority Data

Apr. 4, 2007   (KR) .................. 10-2007-0033411

(51) Int. Cl.
  *A61B 5/021* (2006.01)
  *A61B 5/0402* (2006.01)
  *A61B 5/00* (2006.01)
  *A61B 5/01* (2006.01)
(52) U.S. Cl. ......... 600/485; 600/324; 600/509; 600/549
(58) Field of Classification Search .................. None
  See application file for complete search history.

(56) References Cited

U.S. PATENT DOCUMENTS

| 5,995,858 | A * | 11/1999 | Kinast | 600/323 |
| 2002/0193692 | A1 | 12/2002 | Inukai | |
| 2008/0183232 | A1* | 7/2008 | Voss et al. | 607/24 |
| 2008/0214942 | A1* | 9/2008 | Oh et al. | 600/485 |

FOREIGN PATENT DOCUMENTS

| WO | WO 00/44274 | | 8/2000 |
| WO | WO 02/33846 | A1 | 4/2002 |
| WO | WO 03/094720 | A1 | 11/2003 |

OTHER PUBLICATIONS

Pujary et al. Photodetector size considerations in the design of a noninvasive reflectance pulse oximeter for telemedicine applications. Annual Proceedings of the 29th Annual IEEE Bioengineering conference, pp. 148-149, 2003.*
Jeong et al. A new method to estimate arterial blood pressure using photoplethysmographic signal. Proceedings of the 28th IEEE, EMBS Annual International Conference, New York City, USA, Aug. 30-Sep. 3, 2006.*

* cited by examiner

*Primary Examiner* — Jennifer Dunston
(74) *Attorney, Agent, or Firm* — Fish & Richardson P.C.

(57) ABSTRACT

The blood pressure monitoring apparatus and method are disclosed that can monitor a blood pressure of a subject using an electrocardiogram signal, a pulse wave signal and a body characteristic information of the subject, wherein the electrocardiogram signal and the pulse wave signal of the subject are monitored to remove a noise signal generated from monitoring of the pulse wave signal, allowing monitoring a precise blood pressure of the subject, and calculating the pulse wave analysis information using the monitored pulse wave signal, and using the electrocardiogram signal and the pulse wave signal to calculate a pulse transit time (PPT), and plugging a calculated pulse wave propagation time, pulse wave analysis information and body characteristic information of the subject into a predetermined regression equation to monitor the blood pressure.

22 Claims, 11 Drawing Sheets

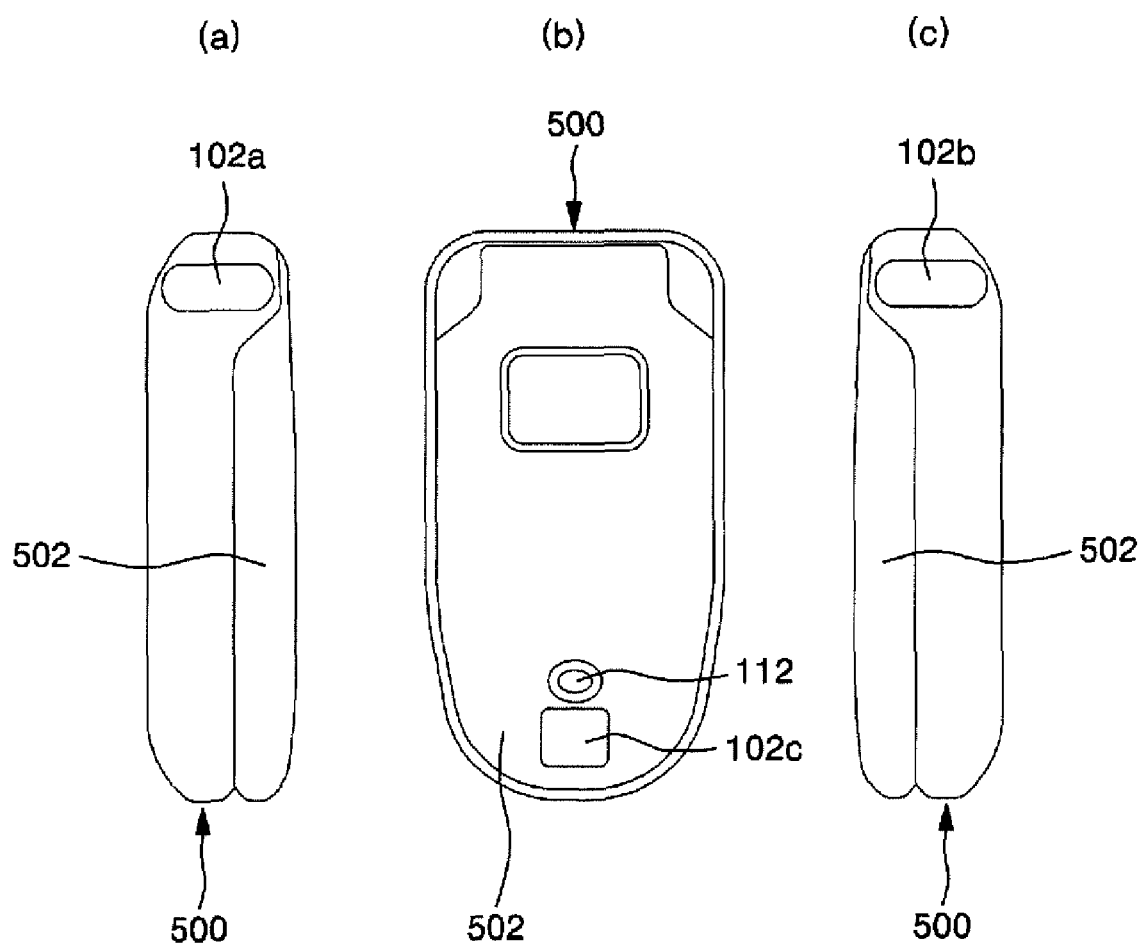

US 8,206,309 B2

BLOOD PRESSURE MONITORING APPARATUS AND METHOD

CROSS-REFERENCE TO RELATED APPLICATION

The present application is based on, and claims priority from, Korean Application Number 10-2007-0033411 filed Apr. 4, 2007, the disclosure of which is incorporated herein by reference in its entirety.

BACKGROUND ART

The following description generally relates generally to a blood pressure monitoring technologies.

Blood pressure is one of the most important vital signs used in the assessment of a (patient's) subject's cardiovascular health. In other words, the blood pressure is one of the most important biological index that contains various health-related information of a patient including cardiac output (CO) defined as the amount of blood ejected by the ventricles of the heart per minute (measured in liters per minute), vascular compliance and physiological changes.

There have been known two existing techniques for monitoring blood pressure, i.e., one is an invasive blood pressure monitoring method and the other is a non-invasive blood pressure monitoring method.

The invasive blood pressure monitoring method is such that a catheter is inserted into an artery and the blood pressure is continuously monitored. The advantage of the invasive blood pressure monitoring method is that the blood pressure can be accurately measured. However, this invasive method of monitoring blood pressure is associated with pain, discomfort and risks of complications to the subject such as infection, thrombosis and air embolism because the catheter must be inserted into an artery at all times.

Noninvasive measurement methods that provide continuous beat-to-beat blood pressure offer an alternative to invasive blood pressure monitoring because they do not carry with them the risk of complications associated with invasive monitoring, as the noninvasive measurement methods measure blood pressure by applying pressure using a blood pressure cuff and monitoring the blood pressure by sound and vibration. Even though they are simple methods to implement, noninvasive measurement methods tend to introduce some inaccuracies.

SUMMARY

In one general aspect, there is provided a blood pressure monitoring apparatus including an electrocardiogram monitoring unit configured to monitor an electrocardiogram signal of a subject; a photoplethysmography (PPG) monitoring unit configured to emit an optical signal of a predetermined frequency to a subject's body, detect an optical signal that has reflected from or penetrated the subject's body, deemphasize noise within the detected optical signal to generate a pulse wave signal; a body characteristic information input unit configured to enable input of body characteristic information of the subject (e.g., at least one of sex, weight, height, length of an arm and age of the subject); a micro computer configured to calculate pulse wave analysis information using the pulse wave signal, to calculate a pulse wave propagation time using the pulse wave signal and the electrocardiogram signal, and to calculate a blood pressure of the subject using the calculated pulse wave analysis information, the pulse wave propagation time and the body characteristic information inputted by the body characteristic information input unit; and a display unit displaying the blood pressure calculated by the micro computer.

Various implementations of this and other aspects also are provided. For example, the electrocardiogram monitoring unit may include electrocardiogram monitoring electrodes configured to monitor an electric signal of the body by being brought into contact with the body; and an electrocardiogram monitoring circuit configured to generate an electrocardiogram signal using the electric signal monitored by the electrocardiogram monitoring electrodes and output the generated electrocardiogram signal to the micro computer.

The PPG monitoring unit may include a PPG sensor configured to generate an optical signal of a predetermined frequency, emit the generated optical signal to the body of the subject, receive an optical signal reflected from the body, and convert the received optical signal to an electric signal; and a PPG monitoring circuit configured to discern a noise signal and a signal of the predetermined frequency from the electric signal converted by the PPG sensor, generate the pulse wave signal using the discerned signal of the predetermined frequency, and input the generated pulse wave signal to the micro computer. The PPG sensor may further include an optical transmitter configured to generate an optical signal of a predetermined frequency and emit the generated optical signal of the predetermined frequency to the body of the subject; and an optical signal receiver configured to receive the optical signal reflected from the body and convert the received optical signal into an electric signal. The apparatus may also include an optical device driving unit configured to drive an optical device of the optical signal transmitter in response to the signal of the predetermined frequency.

The PPG monitoring circuit may include a current/voltage converter configured to convert an output current of the PPG sensor into a voltage; a tuned amplifier configured to tune the voltage converted by the current/voltage converter by a frequency scope that includes a band of a predetermined frequency to remove noise; and a pulse wave extractor configured to mix a signal output by the tuned amplifier with the signal of the predetermined frequency, lowpass filter to extract a pulse wave signal, and output the pulse wave signal to the micro computer. The apparatus may include an analog-to-digital converter configured to convert the pulse wave signal extracted by the pulse wave extractor and output the converted signal to the micro computer, and the pulse wave extractor may include a demodulator configured to multiply the signal output by the tuned amplifier by the signal of the predetermined frequency; and a lowpass filter configured to lowpass filter a signal output by the demodulator to extract a pulse wave signal. The pulse wave extractor, the tuned amplifier and/or the pulse wave extractor may be integrally disposed in the micro computer.

The micro computer may be configured to calculate blood pressure by inputting the pulse wave propagation time, the pulse wave analysis information and the body characteristic information into the following regression equation:

Blood pressure (P)=$k_1 \times$pulse wave propagation time $$+ \sum_i k_{2i} x$$

pulse wave analysis information $$+ \sum_j k_{3j} x$$

body characteristic information, where $k_1$, $K_{2i}$, and $K_{3j}$ define coefficient values respectively corresponding to the pulse wave propagation time, the pulse wave analysis information, and the body characteristic information monitored from the regression analysis, which are predetermined values that are experimentally obtained.

Alternatively, the apparatus may include a temperature sensor configured to monitor a body temperature of a body part from which the pulse wave signal is monitored, and the micro computer may be configured to calculate blood pressure by inputting the pulse wave propagation time, the pulse wave analysis information, the body characteristic information and the body temperature in the following regression equation.

Blood pressure (P)=$k_1$×pulse wave propagation time $$+\sum_i k_{2i} x$$

pulse wave analysis information $$+\sum_j k_{3j} x$$

body characteristic information+$k_4$×body temperature, where $k_1$, $K_{2i}$, $K_{3j}$ and $K_4$ define coefficient values respectively corresponding to the pulse wave propagation time, the pulse wave analysis information, the body characteristic information and the body temperature monitored from the regression analysis, which are predetermined values that are experimentally obtained.

The micro computer may be further configured to compute a second derivative of the pulse wave signal, and to calculate, as pulse wave analysis information a pulse frequency of the subject monitored by the pulse wave signal; and peak values of an acceleration waveform derived from the second derivative of the pulse wave signal.

Storage may be included in the apparatus and configured to store the calculated blood pressure under the control of the micro computer. The storage also may be configured store the body characteristic information of the subject and to enable retrieval of the body characteristic information of the subject from among body characteristic information stored for other subjects responsive to input at the body characteristic information input unit of information corresponding to the subject.

The PPG monitoring unit may be configured to deemphasize noise within the detected optical signal by removing noise, and/or to deemphasize noise within the detected optical signal by emphasizing a component of the detected optical signal other than noise, relative to the noise.

In another general aspect, there is provided a blood pressure monitoring method including inputting body characteristic information of a subject; monitoring an electrocardiogram signal of the subject; emitting an optical signal of a predetermined frequency to the subject's body; detecting an optical signal that has reflected from or penetrated the subject's body; deemphasizing noise within the detected optical signal to generate a pulse wave signal; calculating a pulse wave propagation time and a pulse wave analysis information using the monitored electrocardiogram signal and pulse wave signal; and monitoring the blood pressure of the subject based on the calculated pulse wave propagation time, the pulse wave analysis information and the body characteristic information.

Various implementations of this and other aspects also are provided for this general aspect. For example, the pulse wave signal may be generated by generating an optical signal of a predetermined frequency and emitting the signal to the body of the subject; receiving the optical signal that has penetrated or has been reflected from the body of the subject and converting the signal to an electric signal; tuning the electric signal to a frequency band including the predetermined frequency to deemphasize the noise signal; filtering the tuned electric signal to remove high frequency components; and generating the pulse wave signal based on the mixed and filtered electric signal. Moreover, the pulse wave analysis information may be generated by calculating a pulse frequency of the subject; calculating a second derivative of the pulse wave signal; and calculating peak values of an acceleration waveform derived from the second derivative of the pulse wave signal. Regression formulas indicated with respect to the first general aspect also may be applied.

In accordance with a third general aspect, a blood pressure monitoring apparatus includes an electrocardiogram monitoring unit configured to monitor an electrocardiogram signal of a subject; a photoplethysmography (PPG) monitoring unit configured to emit an optical signal of a predetermined frequency to a subject's body, detect an optical signal that has reflected from or fully penetrated the subject's body, deemphasize noise within the detected optical signal to generate a pulse wave signal; a body characteristic information input unit configured to enable input of body characteristic information of the subject; a micro computer configured to calculate a blood pressure of the subject using the pulse wave signal, the electrocardiogram signal, and the body characteristic information inputted by the body characteristic information input unit; and a display unit displaying the blood pressure calculated by the micro computer. Herein, the micro computer may be further configured to calculate pulse wave analysis information using the pulse wave signal, to calculate a pulse wave propagation time using the pulse wave signal and the electrocardiogram signal, and to calculate the blood pressure of the subject using the calculated pulse wave analysis information and the pulse wave propagation time.

BRIEF DESCRIPTION OF THE DRAWINGS

Various concepts now will be described more fully hereinafter with reference to the accompanying drawings, in which illustrative implementations of the concepts are shown. These concepts may, however, be implemented in many different forms and should not be construed as limited to the implementations set forth herein; rather, these implementations are provided so that this disclosure will be thorough and complete, and will convey aspects of the concepts to those skilled in the art. Like reference numerals refer to the same or similar elements throughout the drawings.

FIGS. 5a, 5b and 5c illustrate a construction of an exemplary implementation of a mobile communication terminal equipped with a blood pressure monitoring apparatus.

DETAILED DESCRIPTION

Figure 1:
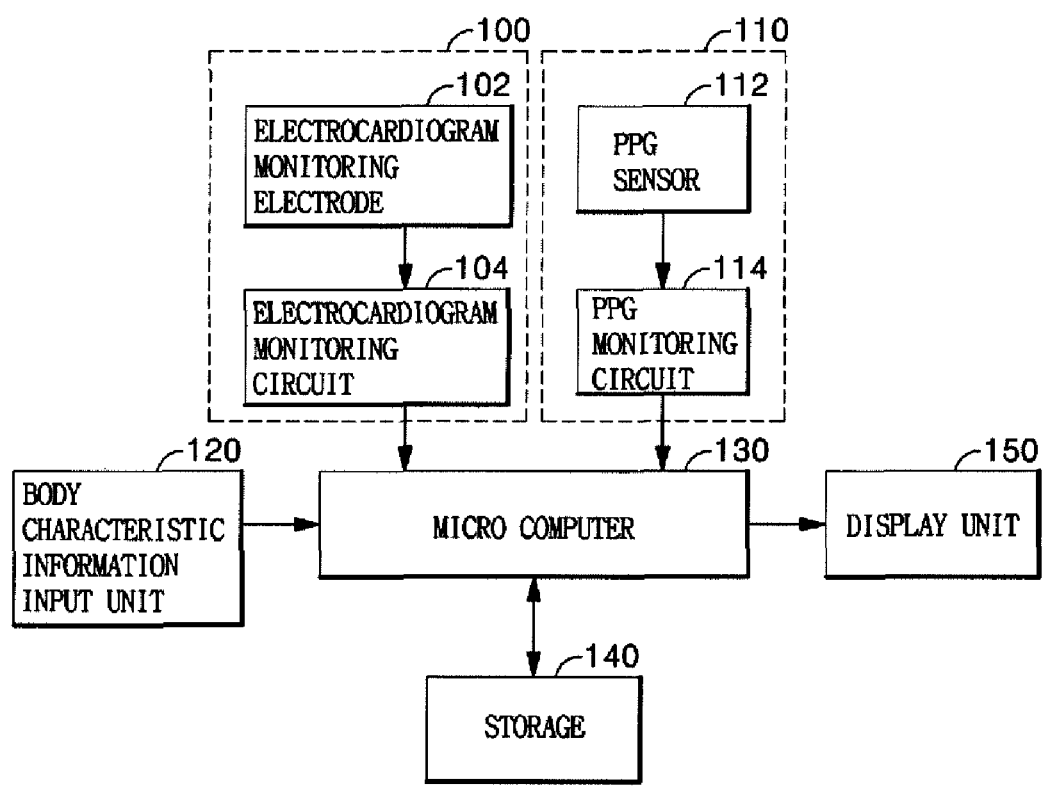
FIG. 1 is a schematic block diagram illustrating an exemplary implementation of a blood pressure monitoring apparatus.

Implementations disclosed hereunder are exemplary only and not intended to be limiting, and serve to explain various principles and techniques. The teaching is susceptible to various modifications and alternative forms, and specific implementations thereof are shown by way of example in the drawings.

FIG. 1 is a schematic block diagram illustrating an exemplary implementation of a blood pressure monitoring apparatus, where reference numeral 100 defines an electrocardiogram monitoring unit for detecting an electrocardiogram signal of a subject.

The electrocardiogram monitoring unit 100 may be operated in such a way that electrocardiogram monitoring electrodes 102 are placed on the skin of a subject's body to detect an electric signal of the body. The electric signal of the body detected by the electrocardiogram monitoring electrodes 102 may be inputted to an electrocardiogram monitoring circuit 104 to detect an electrocardiogram of the subject.

Reference numeral 110 defines a photoplethysmography (PPG) monitoring unit for detecting a pulse wave of the subject. The photoplethysmography (PPG) monitoring unit 110 may be operated in such a manner that a PPG sensor 112 (i.e., PPG finger sensor and PPG ear sensor) is placed on a subject's body, i.e., fingers or ears, to sense the PPG signal of the subject. The PPG signal sensed by the PPG sensor 112 may be inputted to a PPG monitoring circuit 114, whereby a pulse wave signal is monitored.

Reference numeral 120 is a body characteristic information input unit. The body characteristic information input unit 120 may include, for instance, a plurality of functional keys, and the body characteristic information of a subject that needs measurement of blood pressure is inputted by manipulation of the functional keys. The body characteristic information may include, but not limited to, at least any one or more of sex, weight, height, length of an arm and age of a subject.

Reference numeral 130 is a micro computer. The micro computer 130 may use the electrocardiogram signal monitored by the electrocardiogram monitoring unit 100 and the pulse wave signal monitored by the PPG monitoring unit 110 to calculate a pulse transit time and pulse wave analysis information. Furthermore, the micro computer 130 may plug the body characteristic information inputted from the body characteristic information input unit 120, the pulse wave propagation time and the pulse wave analysis information in a predetermined regression equation to calculate the blood pressure.

Reference numeral 140 is storage. The storage 140 may store the blood pressure calculated by the micro computer 130 under the control of the micro computer 130. Furthermore, the storage 140 may store respective body characteristic information of a plurality of subjects inputted from the body characteristic information input unit 120 under the control of the micro computer 130.

If the body characteristic information of the subject is stored in the storage 140 beforehand, the subject stored in the storage 140 may be selected by the manipulation of the functional keys of the body characteristic information input unit 120, and the body characteristic information of the selected subject may be read from the storage 140 and used. Reference numeral 150 is a display unit for allowing the blood pressure calculated by the micro computer 130 to be displayed for visual checks.

Figure 2:
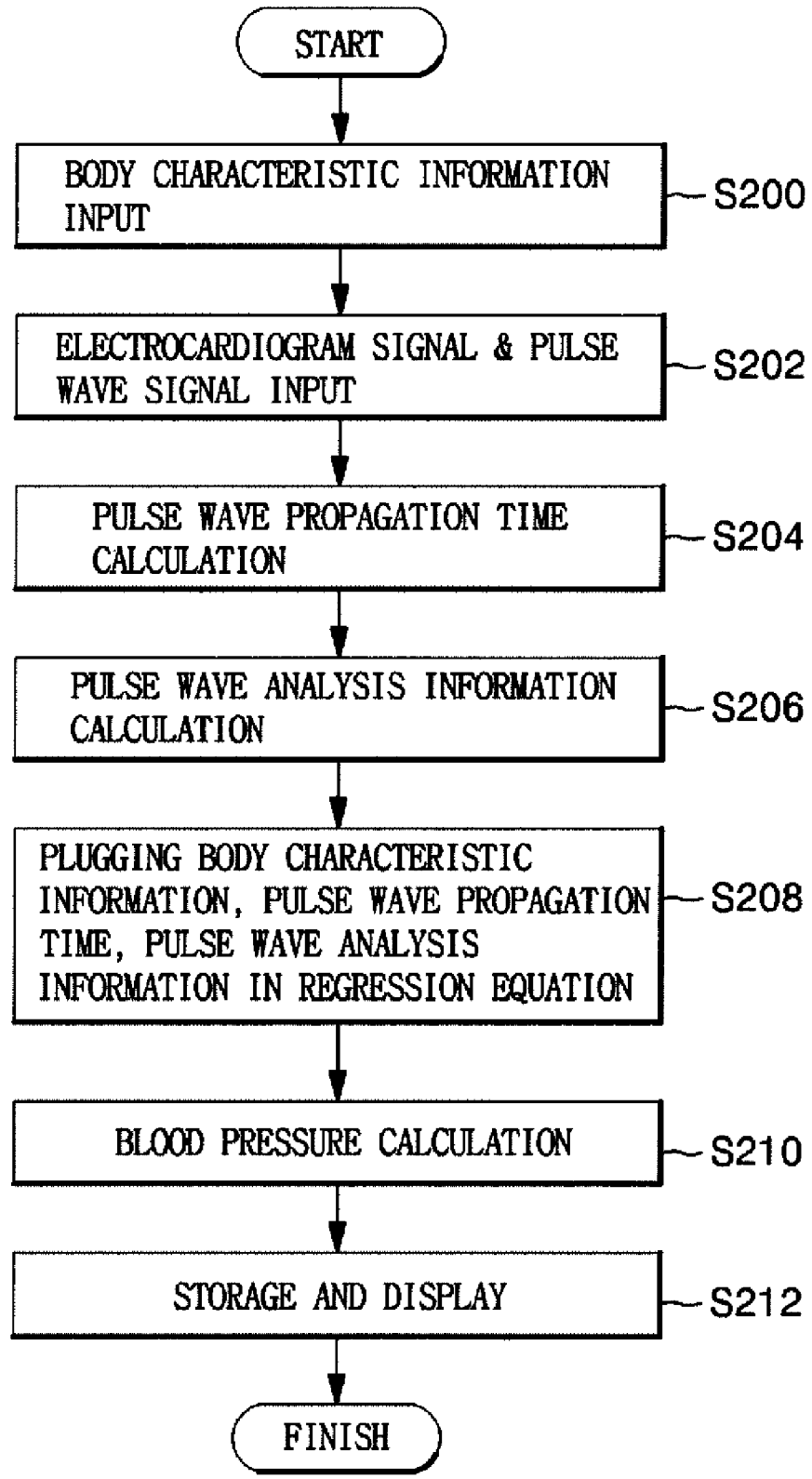
FIG. 2 is a signal flowchart illustrating an exemplary implementation of a blood pressure monitoring method.

FIG. 2 is a signal flowchart illustrating an exemplary implementation of a blood pressure monitoring method.

Referring to FIG. 2, when the blood pressure is to be monitored, the micro computer 130 may input from the body characteristic information input unit 120 the body characteristic information of a subject from whom blood pressure is to be monitored (S200). The body characteristic information may include, but not limited to, at least any one or more of sex, weight, height, length of an arm and age of a subject.

The body characteristic information may be inputted by manipulation of the plurality of functional keys disposed at the body characteristic information input unit 120. If the body characteristic information of the subject is stored in the storage 140 beforehand, the subject stored in the storage may be selected by manipulation of the body characteristic information input unit 120, and the body characteristic information of the selected subject may be inputted from the storage 140.

The micro computer 130 may input the electrocardiogram signal monitored by the electrocardiogram monitoring unit 100 and the pulse wave signal monitored by the PPG monitoring unit 110 (S202).

Once the electrocardiogram signal and the pulse wave signal are inputted, the micro computer 130 uses the electrocardiogram signal and the pulse wave signal to calculate the pulse wave propagation time (S204). The pulse wave propagation time is a time for the blood starting from the heart to reach a peripheral structure such as a finger tip or a toe tip, and may be obtained by R wave of the electrocardiogram signal and pulse wave signal. The detailed operation of calculating the pulse wave propagation time will be described later. A relation between the blood pressure and the pulse wave propagation time may be expressed by the following equation 1.

$$c = \sqrt{\frac{V}{\delta(\partial V/\partial P)}} = \sqrt{\frac{V}{\delta}\frac{\partial P}{\partial V}} \qquad \text{[Equation 1]}$$

where, c is a pulse wave velocity obtained by dividing a distance between the heart and the finger tip by a pulse wave propagation time, $\delta$ is blood density, V is blood volume and P is blood pressure. Assuming that the blood density $\delta$ is constant the Equation 1 may be simply expressed by the following Equation 2.

$$\Delta P \propto c^2 \left(\frac{\Delta V}{V}\right) \qquad \text{[Equation 2]}$$

where, $\Delta P$ is a substitution of $\partial P$, and $\Delta V$ is a substitution of $\partial v$.

As noted from the Equation 2, the changes in blood pressure are proportional to changes of the pulse wave velocity (c) and the blood volume (V), and the pulse wave velocity is related to a distance between the heart and the finger tip and a pulse wave propagation time. Moreover, the blood pressure may be estimated by the pulse wave propagation time and the blood volume.

If the pulse wave propagation time is calculated, the micro computer 130 may analyze the pulse wave signal inputted from the PPG monitoring unit 110 to calculate the pulse wave analysis information (S206). The detailed operation of obtaining the pulse wave analysis information will be described later.

Once the pulse wave propagation time and the pulse wave analysis information are calculated, the micro computer 130 may the substitute the body characteristic information of the subject, the pulse wave propagation time and the pulse wave analysis information into a predetermined regression equation to calculate the blood pressure (S208, S210). Once the blood pressure is calculated, the micro computer 130 may store the calculated blood pressure in the storage 140 for management, and display the blood pressure on the display unit 140 for visual checks (S212).

Now, the blood pressure monitoring apparatus will be described in detail with reference to FIGS. 3, 4a and 4b.

Figure 3:
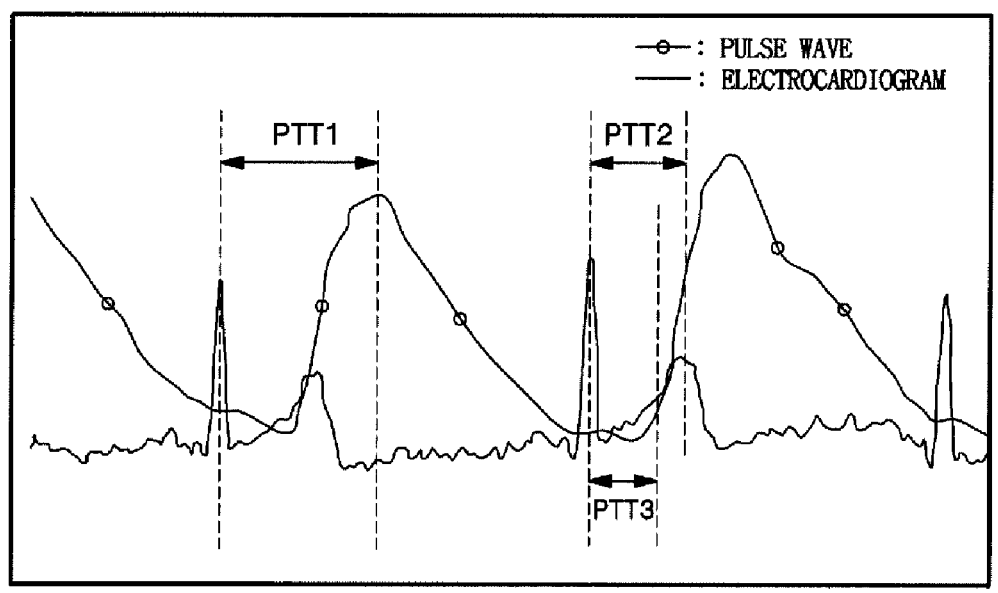
FIG. 3 is a graph showing an electrocardiogram signal and a pulse wave signal.
Figure 4A:
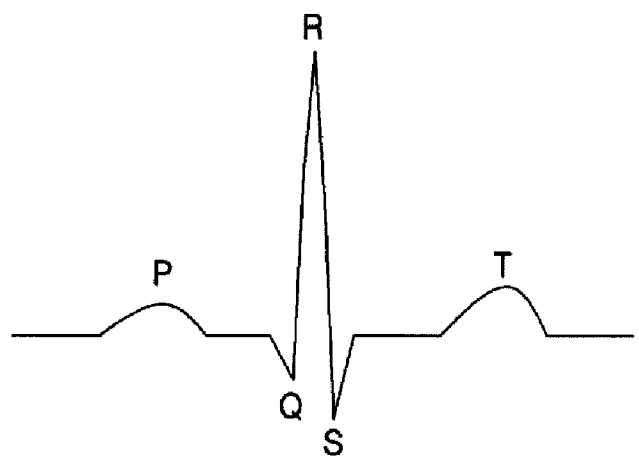
FIG. 4a is a schematic view of a representative electrocardiogram signal.
Figure 4B:
FIG. 4b is a schematic view of a representative pulse wave signal.

FIG. 3 is a graph showing an electrocardiogram signal and a pulse wave signal, FIG. 4a is a schematic view of a representative electrocardiogram signal monitored by an electrocardiogram monitoring unit 100, and FIG. 4b is a schematic view of a representative pulse wave signal monitored from a finger tip of a subject.

Referring to FIG. 4a, the electrocardiogram signal may be divided to a P-wave, a Q-wave, an R-wave, an S-wave and a T-wave according to location of a peak point. The R-wave is a wave detected from a point where blood is charged from heart. The changes of blood volume are generated by repeated diastole and systole of the heart. The PPG monitoring unit 110 may monitor a pulse wave signal that is changed by the changes of blood volume as shown in FIG. 4b.

The micro computer 130 may employ the R-wave of the electrocardiogram signal and the pulse wave signal to obtain the pulse wave propagation time. In order to monitor the pulse wave propagation time, a certain point from the pulse wave signal must be set up as a reference point. The pulse wave propagation time may be calculated by a time between the R-wave of the electrocardiogram signal and the reference point of the set-up pulse wave signal.

For example, as illustrated in FIG. 3, a peak point of the pulse wave signal may be set up as a reference point (REF1), and a time between the set-up reference point (REF1) and the R-wave of the electrocardiogram signal may be determined as the pulse wave propagation time (PTT1). Alternatively, a peak point derived from first derivative of the pulse wave signal may be set up as the reference point (REF2) and a time between the set-up reference point (REF2) and the R-wave of the electrocardiogram signal may be determined as the pulse wave propagation time (PPT2). Alternatively, a peak point derived from second derivative of the pulse wave signal may be set up as a reference point (REF3) and the a time between the set-up reference point (REF3) and the R-wave of the electrocardiogram signal may be determined as the pulse wave propagation time (PPT3).

Figure 4C:
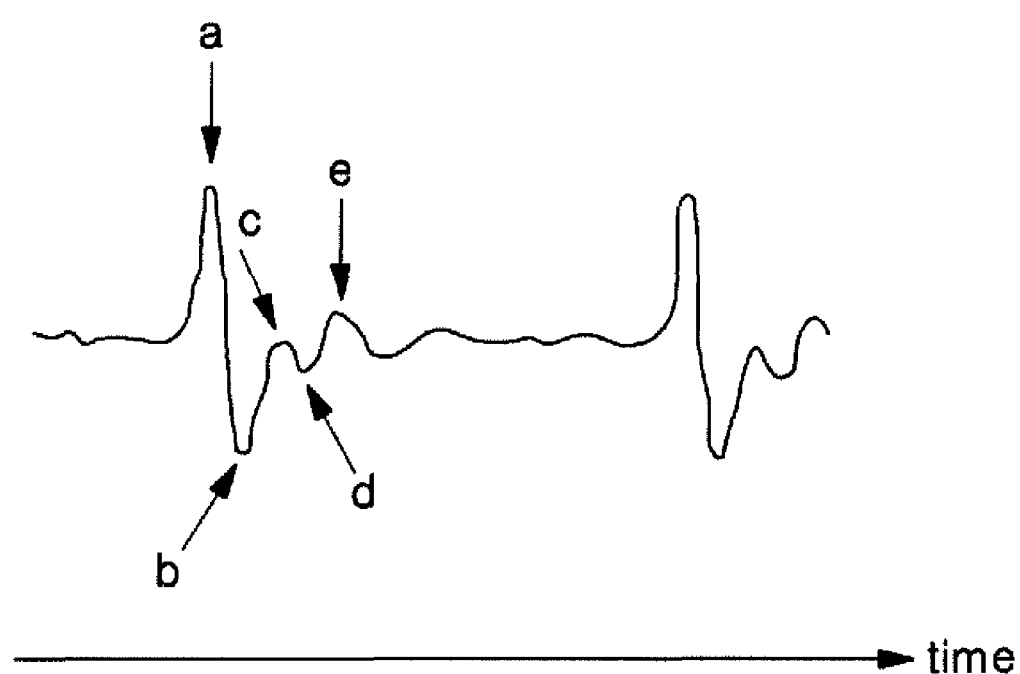
FIG. 4c is a schematic view of a second-derivative of acceleration waveform in a pulse wave signal.

Furthermore, the pulse wave analysis information may be acquired by analyzing waveforms of the pulse wave signal. FIG. 4c is a schematic view of a second-derivative of acceleration waveform in a pulse wave signal.

The micro computer 130 may use values of peak points in the second derivative of acceleration waveform in the pulse wave signal or time differences generated by the peak points to calculate the degree of aging of blood vessel or age of the blood vessel.

The micro computer 130 may divide the values of each peak point to a, b, c, d and e, as illustrated in FIG. 4c, and the divided a, b, c, d and e values are employed to calculate the degree of aging of blood vessel or the aging of the blood vessel.

For example, the micro computer 130 may calculate the degree of aging of blood vessel or the aging of the blood vessel using $$\frac{-b+c+d+e}{a}.$$

The micro computer 130 may take the simple derivative with respect to the pulse wave signal and use a time between the peak points of the first derivative of the pulse wave signal to calculate the pulse frequency (rate). Furthermore, the micro computer 130 may perform the second derivative of the pulse wave signal for conversion to the acceleration waveform and extract values of each peak point, i.e., a, b, c, d and e from the acceleration waveform in the pulse wave signal.

The micro computer 130 may use the pulse frequency and the values of the peak points, i.e., a, b, c, d and e, as the pulse wave analysis information to calculate the blood pressure. If thrombi are accumulated on walls of the blood vessel, a passage through which blood can pass is relatively narrowed, whereby resistance increases to have an effect on the blood pressure, such that the blood pressure may be calculated in consideration of blood states (degree of aging in blood vessel or ages of blood vessel).

The pulse wave signal (i.e., the pulse wave signal monitored from a finger tip) may be affected by the strength of force applied to the PPG sensor 112. The influence to the PPG sensor may be analyzed and solved by the patterns of the monitored pulse wave signal. Alternatively, a pressure sensor may be installed underneath the PPG sensor 112, such that the subject is induced to apply a predetermined force to the PPG 112 and to monitor the pulse wave signal.

Meanwhile, the peripheral structures such as legs, hands or foots of the body may sustain changes in body temperature due to decrease in the amount of blood flow. The pulse wave signal may not be monitored well if temperature is low at a location from which the pulse wave signal is to be monitored, i.e., the finger tip.

Accordingly, a separate temperature sensor is installed adjacent the PPG sensor 112 to allow the PPG sensor 112 to monitor the temperature at the finger tip from which the pulse wave signal is to be monitored, and the monitored temperature may be used as a factor for calculating the blood pressure.

Furthermore, if a temperature lower than the normal body temperature, i.e., lower than 35.5 degrees Celsius, is monitored, the subject is induced to rub or massage a body part having a particular lower temperature and to increase the temperature of the body part up to an average temperature, where the pulse wave signal may be monitored.

The micro computer 130 may use as a predetermined factor for regression equation for calculation of the blood pressure the body characteristic information including, but not limited to, at least any one or more of sex, weight, height, length of an arm and age of a subject. The micro computer 130 may plug the pulse wave propagation time, the pulse wave analysis information, the body characteristic information and the body temperature in the regression equation of the following Equation 3 to calculate the blood pressure (P).

[Equation 3]

Blood pressure (P)=$k_1$×pulse wave propagation time $$+ \sum_i k_{2i} x$$

pulse wave analysis information $$+ \sum_j k_{3j} x$$

body characteristic information+$k_4$×body temperature, where $k_1$, $K_2$, $K_{2i}$, $K_{3j}$ and $K_4$ define coefficient values respectively corresponding to the pulse wave propagation time, the pulse wave analysis information, the body characteristic information and the body temperature monitored from the regression analysis, which are predetermined values that are experimentally obtained.

Although the body temperature may not be plugged in the Equation 3 to calculate the blood pressure, the body temperature may be plugged in for an accurate calculation of the blood pressure. Furthermore, if the subject is induced to monitor the pulse wave signal by rubbing or massaging a body part, i.e., the finger tip, having a particular lower temperature and increasing the temperature of the body part up to an average temperature, the body temperature may not be inserted into the Equation 3 to calculate the blood pressure.

The blood pressure monitoring apparatus may be configured in an independent blood pressure monitoring device. Furthermore, the blood pressure monitoring apparatus may be used as an integral part of a hand-held terminal such as a personal digital assistant (PDA), a portable multimedia player (PMP), a mobile communication terminal or an MP3 player.

When the blood pressure monitoring apparatus is integrally mounted in the mobile communication terminal, the micro computer 130 may be replaced by a micro computer disposed inside the mobile communication terminal. For example, a mobile communication terminal is disposed with a micro computer performing a function of processing one or more digital signals. As a result, the micro computer disposed in the mobile communication terminal may be embodied to monitor the blood pressure utilizing the body characteristic information, the electrocardiogram signal and the pulse wave signal. Furthermore, the body characteristic information input unit 120, the storage 140 and the display unit 150 disposed in the blood pressure monitoring apparatus may be respectively replaced for use by a key pad, a memory and a display unit mounted in the mobile communication terminal. In doing so, the blood pressure may be accurately monitored at a lower cost using the mobile communication terminal.

FIGS. 5a, 5b and 5c illustrate a construction of an exemplary implementation of a mobile communication terminal equipped with a blood pressure monitoring apparatus.

Referring to FIGS. 5a, 5b and 5c, electrocardiogram monitoring electrodes 102a, 102b, 102c in the blood pressure monitoring apparatus may be respectively disposed at left and right lateral surfaces of a body of the mobile communication terminal and external lower surface of a folder 502. The PPG sensor 112 may be disposed at an adjacent location of the electrocardiogram monitoring electrode 102a disposed at an external lower surface of the folder 502.

Under these circumstances, when a subject may grasp to wrap a body 500 of the mobile communication terminal with one hand, two fingers, i.e., a thumb and an index finger may be brought into contact with the electrocardiogram monitoring electrodes 102a, 102b at the left and right lateral surfaces of the body. Another finger, i.e., a middle finger, may be brought into contact with both the electrocardiogram monitoring electrodes 102a at the lower part of the folder 502 and the PPG sensor 112 to simultaneously monitor the electrocardiogram signal and the pulse wave signal.

Although it is not illustrated in the drawings, a left lateral surface of the body of the mobile communication terminal may be disposed with the electrocardiogram monitoring electrodes 102a, 102b, and the right lateral surface of the body of the mobile communication terminal may be disposed with the remaining electrocardiogram monitoring electrode 102c and the PPG sensor 112. Under these circumstances, each finger, i.e., index fingers from both hands) of the subject may be brought into contact with the electrocardiogram monitoring electrodes 102c, 102b, 102c and the PPG sensor 112 to allow monitoring the pulse wave signal. The number of electrocardiogram monitoring electrodes that are used for monitoring the pulse wave signal may be three, or may be two. The locations of electrocardiogram monitoring electrodes 102c, 102b, 102c and the PPG sensor 112 may be changed according to the configuration of the mobile communication terminal.

When the blood pressure monitoring apparatus is integrally mounted in the mobile communication terminal, the electrocardiogram signal, the pulse wave signal and the blood pressure of a subject may be monitored using the mobile communication terminal. Furthermore, a user interface, an operating function and display function of the mobile communication terminal may be utilized to monitor the electrocardiogram signal, the pulse wave signal and the blood pressure of a subject and to display on the display unit 150, whereby a health status of a subject may be automatically checked. Still furthermore, the electrocardiogram signal, the pulse wave signal and the blood pressure of a subject may be utilized to provide a predetermined service including, but not limited to, a moody music such as classic music when the blood pressure or the stroke of pulse increases, a text message notifying a health state or a voice service.

In the blood pressure monitoring apparatus and method in the foregoing exemplary implementations, the PPG sensor 110 may generate noise signals amid the monitoring of the pulse wave signal, and the generated noise signals may increase the power consumption, resulting in an inaccurate monitoring of the pulse wave signal and subsequently an inaccurate measurement of the blood pressure. Therefore, the noise signals are preferably removed that are generated in the course of monitoring of the pulse wave signals to accurately detect the blood pressure.

Now, exemplary implementations of the blood pressure monitoring apparatus and method capable of removing noise signals generated from the monitoring of the pulse wave signal to reduce the power consumption, and enhancing the signal-to-noise (S/N) ratio will be described in detail with reference to FIGS. 6 to 10.

Figure 6:
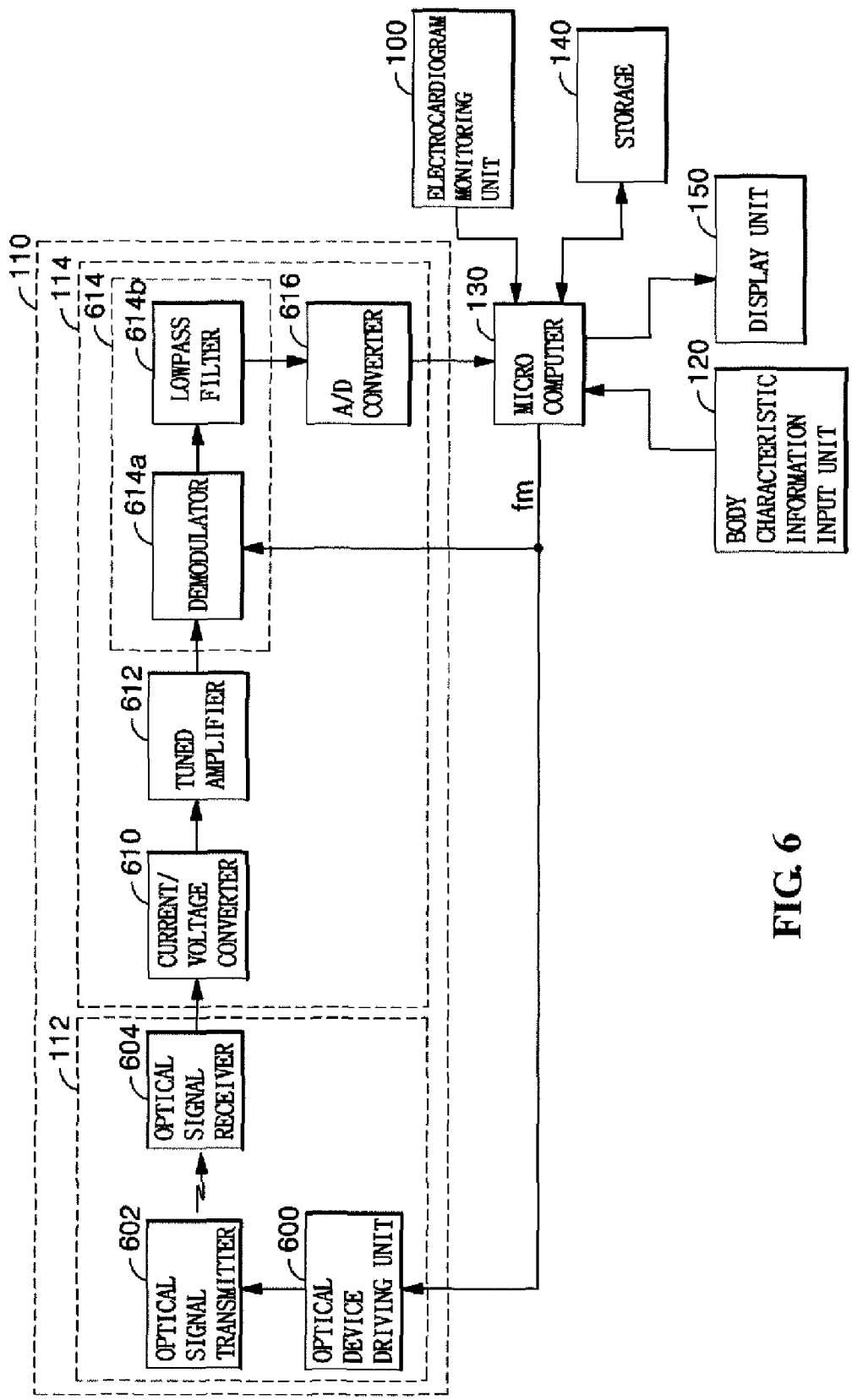
FIG. 6 is a schematic block diagram illustrating another exemplary implementation of a blood pressure monitoring apparatus.

FIG. 6 is a schematic block diagram illustrating another exemplary implementation of a blood pressure monitoring apparatus, wherein the PPG sensor 12 is comprised of a light emitting device driving unit 600, an optical signal transmitter 602 and an optical signal receiver 604.

The light emitting device driving unit 600 may drive an optical device (not shown) disposed at the optical signal transmitter 602 to output an optical signal in response to an oscillation signal of a particular frequency (fm) outputted by the micro computer 130. For example, the micro computer 130 may generate an oscillation signal having a frequency (fm) of 300 MHz or more, whereby the light emitting device driving unit 600 drives the optical device of the optical signal transmitter 602 to generate an optical signal in response to the oscillation signal.

The optical device of the optical signal transmitter 602 may use, for example, a near infrared generating light emitting diode for generating the near infrared to generate the optical signal. The optical signal outputted from the optical signal transmitter 602 is emitted toward a subject. The optical signal outputted from the optical signal transmitter 602 is not the general direct current optical signal but an optical signal of a particular frequency generated by the micro computer 130 for removing the noise. For example, the optical signal generated by the optical signal transmitter 602 is an optical signal having a frequency (fm) of 300 MHz or more.

Therefore, even if part of the optical signal outputted from the optical signal transmitter 602 is absorbed by the body of a subject, and the remaining of the optical signal penetrates or is reflected from the body, the penetrated or reflected optical signal still holds the particular frequency (fm).

The optical signal of a particular frequency that has penetrated or reflected from the body may be received by the optical signal receiver 604 and converted to an electric signal, and the converted electric signal may be outputted to the PPG monitoring circuit 114. The PPG monitoring circuit 114 may be a photo diode or a phototransistor. The photo diode or phototransistor may convert the optical signal of a particular frequency (fm) received by the photo diode or the phototransistor to a current signal of a particular frequency, where the phototransistor to a current signal of a particular frequency may be outputted to the PPG monitoring circuit 114.

The PPG monitoring circuit may include a current/voltage converter 610, a tuned amplifier 612, a pulse wave extractor 614 and analog-to-digital (A/D) converter 616, where the pulse wave extractor 614 may include a demodulator 614a and a lowpass filter 614b.

The current signal of a particular frequency received and outputted by the optical signal receiver 604 may be converted to a voltage signal of a particular frequency by the current/voltage converter 610 of the PPG monitoring circuit 114 and inputted to the tuned amplifier 612.

The signal of a particular frequency outputted by the current/voltage converter 610 may be tuned and amplified by the tuning amplifier 612.

It should be noted that only a signal of particular frequency out of the signals outputted from the current/voltage converter 610 may be tuned by the tuned amplifier 612, while a signal having no particular frequency, i.e., noise signal, may not be tuned by the tuning amplifier 612 but be removed of the noise signal.

The output signal of the tuning amplifier 612 is inputted to the demodulator 614a of the pulse wave extractor 614, where the demodulator 614a may multiply the output signal of the tuning amplifier 612 by an oscillation signal of a particular frequency outputted from the micro computer 130 and demodulated.

The output signal of the demodulator 614a may be filtered by the lowpass filter 614b to be removed of the noise signal from where a pulse wave signal is monitored. The monitored pulse wave signal may be converted to a digital signal by the A/D converter 616 to be inputted to the micro computer 130. The A/D converter 616 may be integrally mounted in the micro computer 130.

In other words, the blood pressure monitoring apparatus according to another exemplary implementation is configured in such a manner that a noise signal is initially removed by the tuning amplifier 612 when monitoring the pulse wave signal, and the noise signal may be secondly removed by the pulse wave extractor 614 to be converted to the digital signal by the A/D converter 616 and inputted to the micro computer 130. Therefore, the noise signal generated in the course of monitoring the pulse wave signal can be removed to reduce the consumed power and to enhance the signal-to-noise ratio.

If the micro computer 130 is integrally disposed with the function of converting the analog signal to the digital signal, the A/D converter 616 may not be disposed in the PPG monitoring circuit and the output signal of the lowpass filter 614b may be directly inputted to the micro computer 130.

The electrocardiogram monitoring unit 100 may monitor the electrocardiogram signal of the subject and input to the micro computer 130, and the body characteristic information input unit 120 may input the body characteristic information of the subject to the micro computer 130 according to manipulation of a user.

Successively, the micro computer 130 may utilize the pulse wave signal and the electrocardiogram signal of the subject to calculate the pulse wave propagation time and the pulse wave analysis information, where the calculated pulse wave propagation time, the pulse wave analysis information and body characteristic information are plugged in the Equation 3 to monitor the blood pressure of the subject.

Once the blood pressure of the subject is monitored, the micro computer 130 may store and manage the monitored blood pressure in the storage 140 and display on the display unit 150 to allow a user to check.

Contemplated implementations include a bio-signal monitoring apparatus for monitoring various bio-signals of a subject by using the pulse wave signal monitored by the PPG monitoring circuit 114. For example, the micro computer 130 may use the pulse wave signal to monitor not only the basic bio signals but body fat, body water, body heat, body composition and bone mineral density (BMD), and may be widely used for monitoring sugar content in fruits, an inner composition analysis of a plant or discrimination of various kinds of materials. To this end, the micro computer 130 may be mounted with various systems such as arithmetic algorithm, database and look-up table for providing results derived from various kinds of detections (pulse wave signals inputted to the micro computer 130), so that a variety of detection values may be comprehensively realized.

A blood pressure monitoring apparatus according to another exemplary implementation may remove the direct current offset or outside optical noise. i.e., fluorescent lamp noise of 60 Hz or high frequency noises of 120 Hz, using the PPG monitoring circuit 114 without causing any distortion to the pulse wave signal. Because the pulse wave signal is monitored with the noises being separated, a high signal-to-noise ratio may be maintained even if the intensity of optical signal outputted by the optical signal transmitter 602 in the PPG sensor 112 is low.

Furthermore, reduced power consumption in the optical signal transmitter 602 (where most of the power is consumed in the blood pressure monitoring apparatus) may enable a markedly reduced overall consumption of power in the blood pressure monitoring apparatus, whereby a low capacity battery may be used to increase the portability of the apparatus FIGS. 7a to 7d illustrate waveforms of an output signal for each part of a photoplethysmography (PPG) monitoring unit in another exemplary implementation.

The light emitting device driving unit 600 may drive the optical device of the optical signal transmitter 602 to generate an optical signal having a predetermined frequency (fm) in response to the predetermined frequency (fm) outputted from the micro computer 130, and the generated optical signal penetrates or is reflected from the body of a subject. The optical signal that has penetrated or been reflected from the body may be received by the optical signal receiver 604 and converted to an electric signal. The signal outputted by the optical signal receiver 604 is a current signal, which is in turn converted to a voltage signal by the current/voltage converter 610 of the PPG monitoring circuit 114.

Figure 7A:
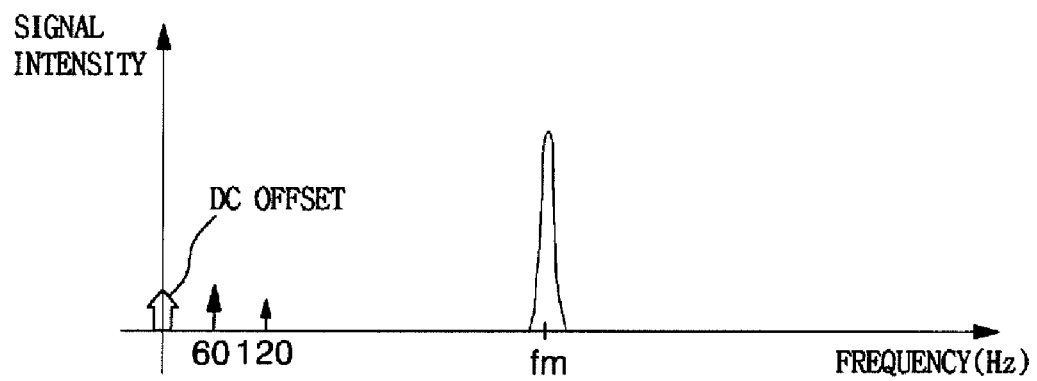
FIGS. 7a to 7d illustrate waveforms of an output signal for each part of a photoplethysmography (PPG) monitoring unit in another exemplary implementation.

Referring to FIG. 7a, the voltage signal converted by the current/voltage converter 610 may include various mixed noise signals including a direct current offset noise signal, an outside optical noise signal (i.e., 60 Hz or 120 Hz) besides the optical signal (the optical signal reflected from the body) converted to a predetermined frequency (fm).

The optical signal transmitter 602 may generate an optical signal having a predetermined frequency (fm), i.e., a frequency of 300 Hz or more, to allow the optical signal having the predetermined frequency (fm) to be separated from the generated noise signals.

Figure 7B:
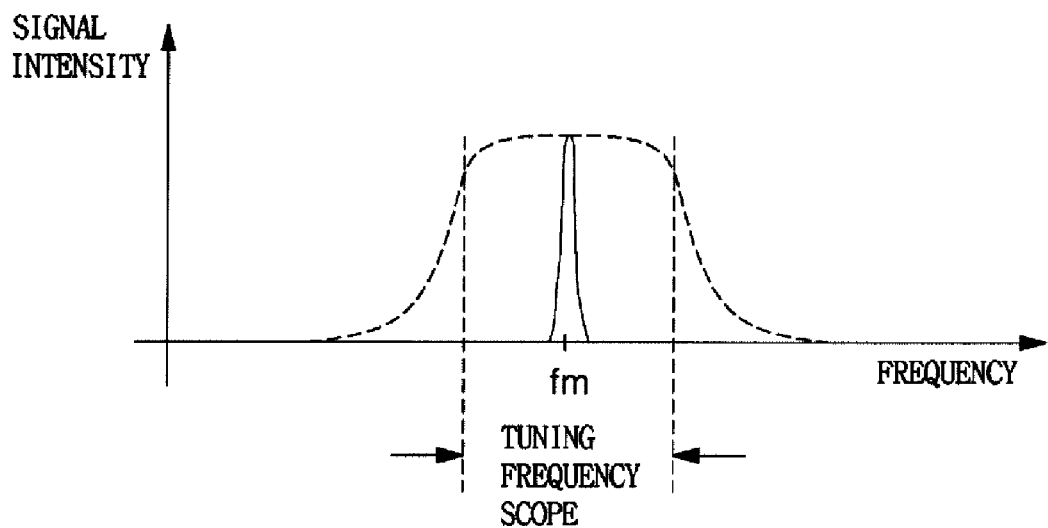

The output signal of the current/voltage converter 610 is inputted to the tuned amplifier 612 to be tuned and amplified. The tuning frequency scope of the tuned amplifier 612 may include the predetermined frequency as shown in FIG. 7b. The signal having the predetermined frequency (fm) in the output signal of the current/voltage converter 610 is tuned and amplified by the tuned amplifier 612, and the direct current offset noise signal and the outside optical noise signal in the output signal of the current/voltage converter 610 are typically not tuned only to be removed thereafter.

The signal tuned by the tuned amplifier 612 may be outputted without being amplified, or may be outputted by being amplified as much as a predetermined magnification factor. The amplification in the tuned amplifier 612 is to enhance the quantization precision when the signal inputted to the micro computer 130 is converted to a digital signal.

Figure 7C:
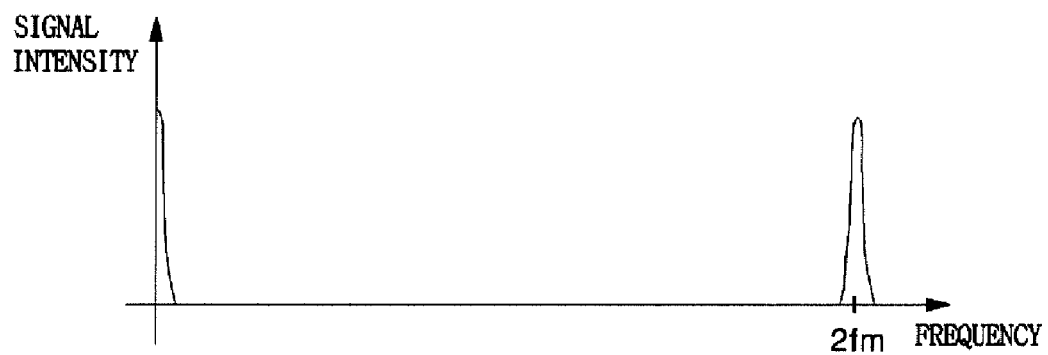
Figure 7D:
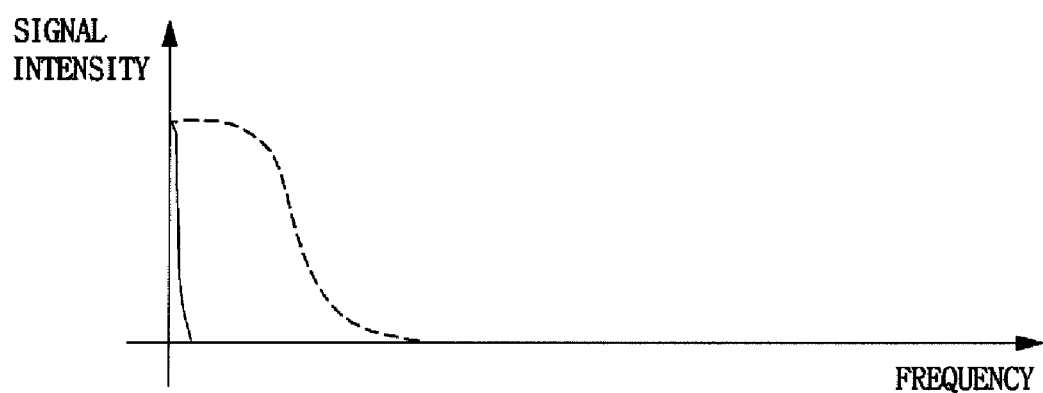

The signal tuned by the tuned amplifier 612 is inputted to the demodulator 614a and demodulated as illustrated in FIG. 7c. The demodulator 614 may be, for example, a mixer, where the demodulation is performed by multiplying the output signal of the tuned amplifier 612 by the signal of a predetermined frequency (fm) outputted by the micro computer 130. In fact, the signal demodulated by the demodulator 614a may include a signal of direct current domain and a high frequency having a frequency (2 fm) twice the predetermined frequency (fm), as shown in FIG. 7c.

The output signal from the demodulator 614a may be inputted to the lowpass filter 614b and filtered. A passband of the lowpass filter 614b may be set up as shown in dotted line of FIG. 7d. In doing so, only the signal of the direct current domain may pass the lowpass filter 614b to be converted to a digital signal by the A/D converter 616 and inputted to the micro computer 130, and the high frequency having the frequency (2 fm) twice the predetermined frequency (fm) may be blocked by the lowpass filter 614b and may not be inputted to the micro computer 130.

Figure 8:
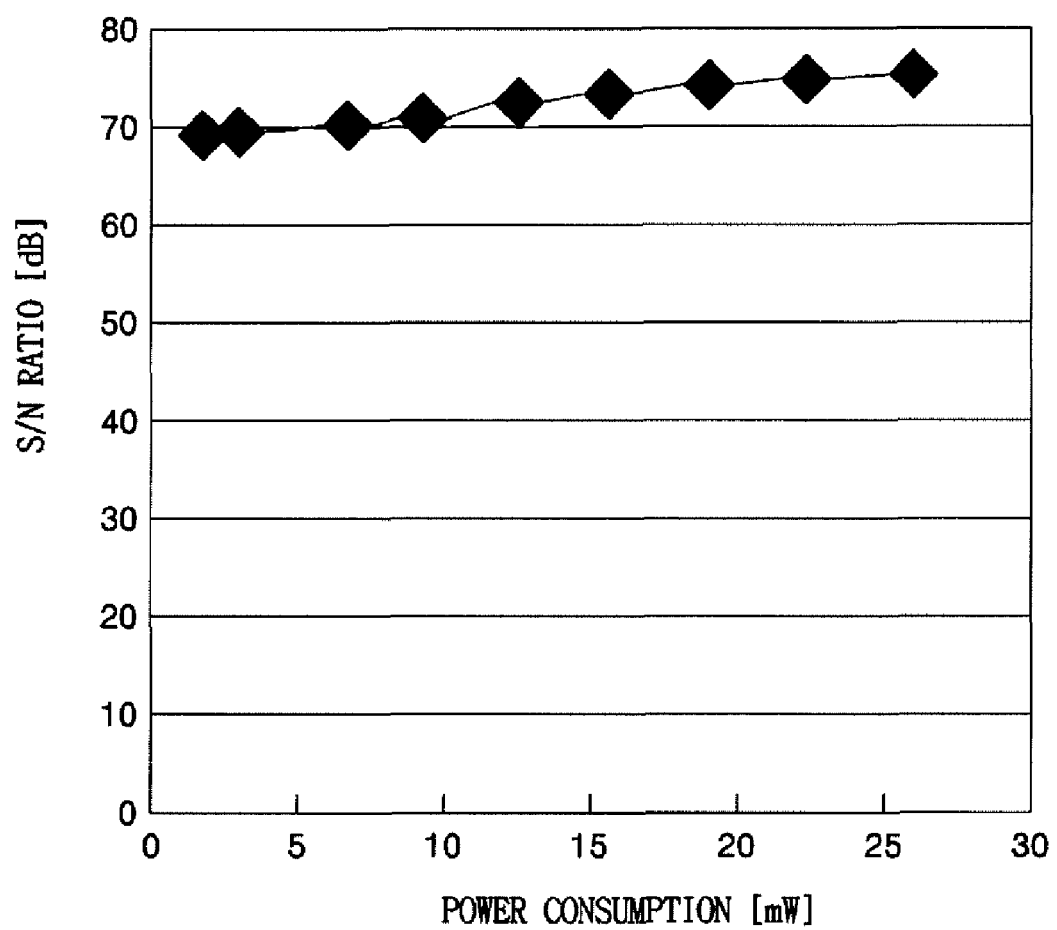
FIG. 8 is a schematic view of a signal to noise ratio relative to a power consumption of a blood pressure monitoring apparatus in another exemplary implementation.

FIG. 8 is a schematic view of a signal to noise ratio relative to a power consumption of a blood pressure monitoring apparatus in another exemplary implementation.

Now, it can be noted from FIG. 8 that the signal-to-noise ratio relative to the power consumption by the optical signal transmitter 602 that outputs an optical signal shows a gentle curve. For example, if the power consumption of the optical signal transmitter 602 is limited to 5 mW, the signal-to-noise ratio is approximately 70 dB. Furthermore, even if the power consumption of the optical signal transmitter 602 is reduced, the signal-to-noise ratio may not be greatly changed but instead still reaches approximately 70 dB. As a result, it can be noted that a precise pulse wave signal can be obtained even if the power consumption is reduced by setting up a low driving power of the optical signal transmitter 602.

Figure 9:
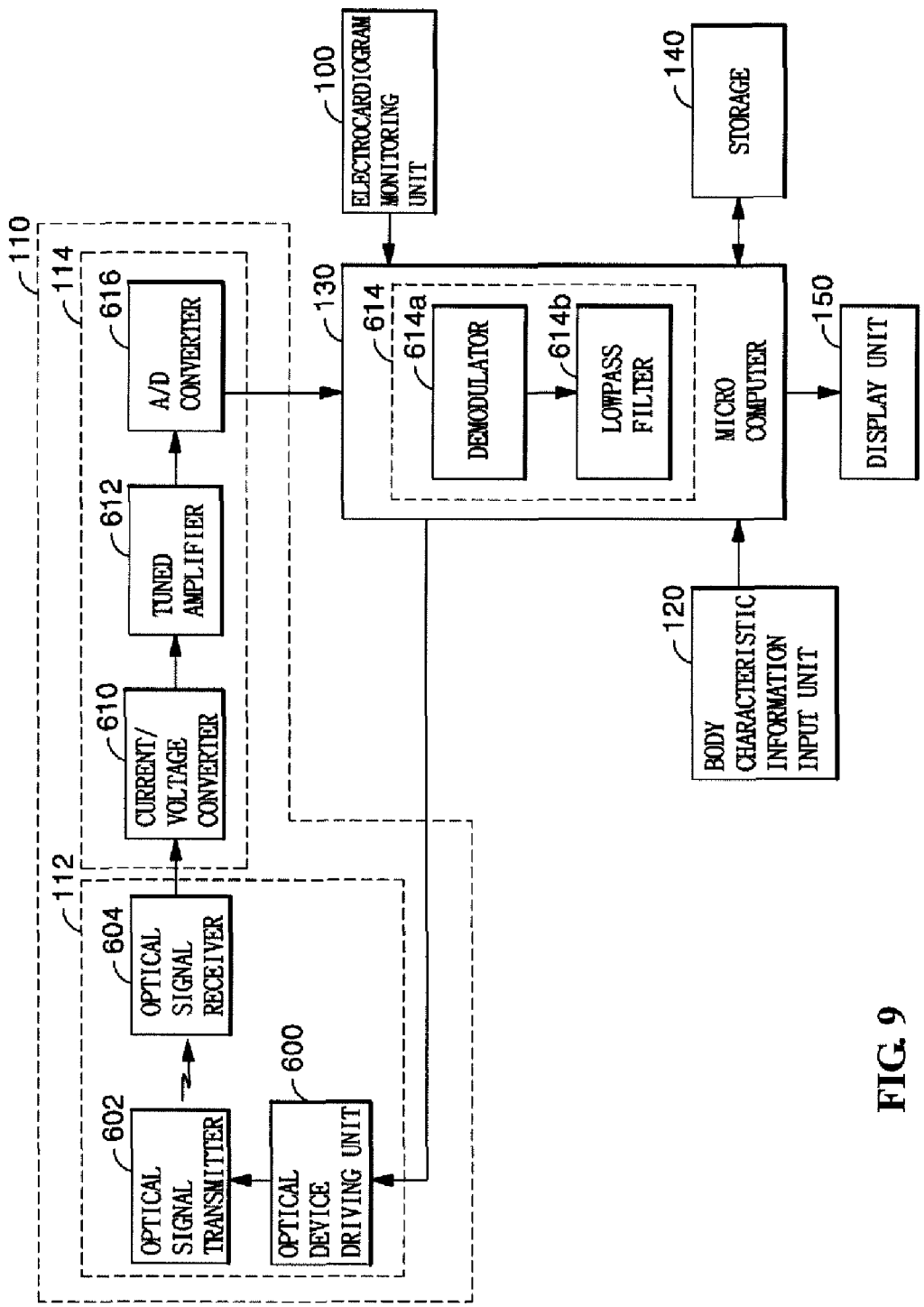
FIG. 9 is a schematic block diagram illustrating a construction of still another exemplary implementation of a blood pressure monitoring apparatus.

FIG. 9 is a schematic block diagram illustrating a construction of still another exemplary implementation of a blood pressure monitoring apparatus, where the apparatus may comprise a micro computer 130 integrally comprised of a pulse wave extractor 614 including a demodulator 614a and a lowpass filter 614b.

If the demodulator 614a and the lowpass filter 614b are integrally disposed inside the micro computer 130, the micro computer 130 may demodulate the digital signal inputted from the A/D converter 616 by the conventional arithmetic algorithm function. The micro computer 130 may use a finite impulse response (FIR) filter or an infinite impulse response (IIR) filter as the lowpass filter 614b to block the high frequency signal.

Figure 10:
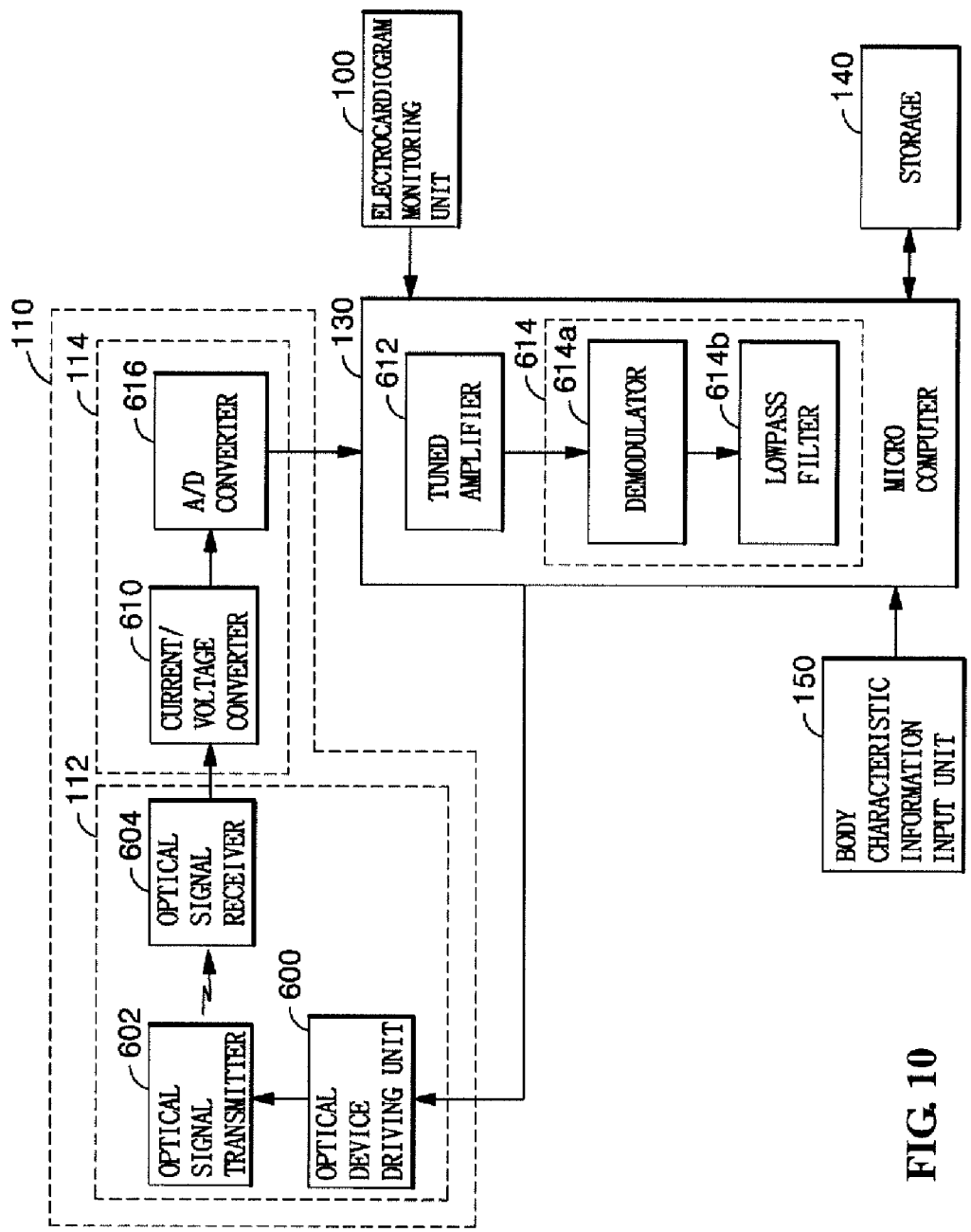
FIG. 10 is a schematic block diagram illustrating a construction of still another exemplary implementation of a blood pressure monitoring apparatus.

FIG. 10 is a schematic block diagram illustrating a construction of still another exemplary implementation of a blood pressure monitoring apparatus, where the apparatus may comprise a micro computer 130 integrally comprised of a tuned amplifier 612, demodulator 614a and a lowpass filter 614.

As apparent from the foregoing, the blood pressure monitoring apparatus and method according to the instant teaching can monitor an electrocardiogram signal and a pulse wave signal of a subject to calculate a pulse wave propagation time and pulse wave analysis information, and the calculated pulse wave propagation time, pulse wave analysis information and body characteristic information are used to monitor the blood pressure of the subject. The apparatus and method are non-invasive and capable of monitoring the blood pressure without recourse to cuff.

An optical signal modulated by a particular frequency is emitted to a body of a subject, and the optical signal reflected from the body can be tuned, demodulated and lowpass filtered to remove noise signals generated in the course of monitoring the pulse wave signal, to enhance a signal-to-noise ratio, to reduce the power consumption and to increase the monitoring accuracy of the blood pressure.

A tuned amplifier and a pulse wave extractor can be integrally disposed in a micro computer to reduce the size of the blood pressure monitoring apparatus and to enhance the portability of the apparatus.

Thus, a blood pressure monitoring apparatus and method is contemplated for monitoring an electrocardiogram signal, a pulse wave signal, and the blood pressure of the subject, safely and with high accuracy, in continuous manner using the monitored electrocardiogram and pulse wave signals and body characteristic information of the subject, without giving load on the subject. Also, at least one implementation of the disclosed blood pressure monitoring apparatus and method can obviate the noise generated in the course of monitoring the pulse wave to improve a signal-to-noise (S/N) ratio, substantially reduce the power consumption and enhance the monitoring accuracy of the blood pressure.

Moreover, according to one implementation, electrocardiogram and pulse wave signals of a subject are monitored. Specifically, the electrocardiogram signal is monitored by using a plurality of electrocardiogram monitoring electrodes placed on the skin of a subject body. And, the pulse wave signal is monitored in such a manner that a photoplethysmography (PPG) sensor generates a predetermined frequency of optical signal and emits the optical signal to a subject's body, where the signal is directed onto an area of the skin so that it penetrates or reflects from the tissue. This optical signal that has penetrated or reflected is received and converted to an electric signal. The converted electric signal is synchronized with a frequency band including a predetermined frequency to be removed of a noise signal, demodulated and filtered, whereby a pulse wave signal free of radio frequency is monitored.

Also according to this implementation, a pulse wave propagation time is calculated using the detected electrocardiogram and pulse wave signals, the pulse wave signal is analyzed to calculate pulse wave analysis information, and the calculated pulse wave propagation time, pulse wave analysis information and body characteristic information of the subject are substituted into a predetermined regression equation to monitor the blood pressure.

Accordingly, exemplary implementations as described herein are illustrative, and should not to be construed as limiting. Although the exemplary implementations have been described, many modifications and variations are possible in the exemplary implementations. Therefore, all such modifications are intended to be included within the scope of that which is set forth in this disclosure.

What is claimed is:

1. A blood pressure monitoring apparatus comprising:
an electrocardiogram monitoring unit configured to monitor an electrocardiogram signal of a subject;
a photoplethysmography (PPG) monitoring unit configured to emit an optical signal of a predetermined frequency to a subject's body, detect an optical signal that has reflected from or penetrated the subject's body, and deemphasize noise within the detected optical signal to generate a pulse wave signal;
a body characteristic information input unit configured to enable input of body characteristic information of the subject;
a micro computer configured to calculate pulse wave analysis information using the pulse wave signal, to calculate a pulse wave propagation time using the pulse wave signal and the electrocardiogram signal, and to calculate a blood pressure of the subject using the calculated pulse wave analysis information, the pulse wave propagation time, and the body characteristic information inputted by the body characteristic information input unit, wherein the micro computer is configured to calculate the blood pressure by inputting the pulse wave propagation time, the pulse wave analysis information and the body characteristic information into the following regression equation:

$$\text{Blood pressure } (P) = k_1 \times \text{pulse wave propagation time} + \sum_i k_{2i} \times \text{pulse wave analysis information} + \sum_j k_{3j} \times \text{body characteristic information}$$

where $k_1$, $K_{2i}$, and $K_{3j}$ define coefficient values respectively corresponding to the pulse wave propagation time, the pulse wave analysis information, and the body characteristic information monitored from the regression analysis, which are predetermined values that are experimentally obtained; and
a display unit displaying the blood pressure calculated by the micro computer.

2. The apparatus as claimed in claim 1, wherein the electrocardiogram monitoring unit comprises:
electrocardiogram monitoring electrodes configured to monitor an electric signal of the body by being brought into contact with the body; and
an electrocardiogram monitoring circuit configured to generate an electrocardiogram signal using the electric signal monitored by the electrocardiogram monitoring electrodes and output the generated electrocardiogram signal to the micro computer.

3. The apparatus as claimed in claim 1, wherein the PPG monitoring unit comprises:
a PPG sensor configured to generate an optical signal of a predetermined frequency, emit the generated optical signal to the body of the subject, receive an optical signal reflected from the body, and convert the received optical signal to an electric signal; and
a PPG monitoring circuit configured to discern a noise signal and a signal of the predetermined frequency from the electric signal converted by the PPG sensor, generate the pulse wave signal using the discerned signal of the predetermined frequency, and input the generated pulse wave signal to the micro computer.

4. The apparatus as claimed in claim 3, wherein the PPG sensor comprises:
an optical transmitter configured to generate an optical signal of a predetermined frequency and emit the generated optical signal of the predetermined frequency to the body of the subject; and
an optical signal receiver configured to receive the optical signal reflected from the body and convert the received optical signal into an electric signal.

5. The apparatus as claimed in claim 4, further comprising an optical device driving unit configured to drive an optical device of the optical signal transmitter in response to the signal of the predetermined frequency.

6. The apparatus as claimed in claim 3, wherein the PPG monitoring circuit comprises:
a current/voltage converter configured to convert an output current of the PPG sensor into a voltage;
a tuned amplifier configured to tune the voltage converted by the current/voltage converter by a frequency scope that includes a band of a predetermined frequency to remove noise; and
a pulse wave extractor comprising a demodulator and a lowpass filter, the pulse wave extractor configured to mix a signal output by the tuned amplifier with the signal of the predetermined frequency, lowpass filter to extract a pulse wave signal, and output the pulse wave signal to the micro computer.

7. The apparatus as claimed in claim 6, further comprising an analog-to-digital converter configured to convert the pulse wave signal extracted by the pulse wave extractor and output the converted signal to the micro computer.

8. The apparatus as claimed in claim 6, wherein:
the demodulator is configured to multiply the signal output by the tuned amplifier by the signal of the predetermined frequency; and
the lowpass filter is configured to lowpass filter a signal output by the demodulator to extract a pulse wave signal.

9. The apparatus as claimed in claim 6, wherein the pulse wave extractor is integrally disposed in the micro computer.

10. The apparatus as claimed in claim 6, wherein the tuned amplifier and the pulse wave extractor are integrally disposed in the micro computer.

11. The apparatus as claimed in claim 1, wherein the body characteristic information includes at least one of sex, weight, height, length of an arm and age of the subject.

12. The apparatus as claimed in claim 1, wherein the micro computer is further configured to compute a second derivative of the pulse wave signal, and to calculate, as pulse wave analysis information:
a pulse frequency of the subject monitored by the pulse wave signal; and
peak values of an acceleration waveform derived from the second derivative of the pulse wave signal.

13. The apparatus as claimed in claim 1, further comprising storage configured to store the calculated blood pressure under the control of the micro computer.

14. The apparatus as claimed in claim 1, further comprising storage configured to store the body characteristic information of the subject, and to enable retrieval of the body characteristic information of the subject from among body characteristic information stored for other subjects responsive to input at the body characteristic information input unit of information corresponding to the subject.

15. The apparatus as claimed in claim 1, wherein the PPG monitoring unit is configured to deemphasize noise within the detected optical signal by removing noise.

16. The apparatus as claimed in claim 1, wherein the PPG monitoring unit is configured to deemphasize noise within the detected optical signal by emphasizing a component of the detected optical signal other than noise, relative to the noise.

17. A blood pressure monitoring apparatus comprising:
an electrocardiogram monitoring unit configured to monitor an electrocardiogram signal of a subject;
a photoplethysmography (PPG) monitoring unit configured to emit an optical signal of a predetermined frequency to a subject's body, detect an optical signal that has reflected from or penetrated the subject's body, and deemphasize noise within the detected optical signal to generate a pulse wave signal;
a body characteristic information input unit configured to enable input of body characteristic information of the subject
a temperature sensor configured to monitor a body temperature of a body part from which the pulse wave signal is monitored;
a micro computer configured to calculate pulse wave analysis information using the pulse wave signal, to calculate a pulse wave propagation time using the pulse wave signal and the electrocardiogram signal, and to calculate a blood pressure of the subject using the calculated pulse wave analysis information, the pulse wave propagation time, the body characteristic information inputted by the body characteristic information input unit, and the body temperature, wherein the micro computer is configured to calculate blood pressure by inputting the pulse wave propagation time, the pulse wave analysis information, the body characteristic information and the body temperature in the following regression equation:
blood pressure (P)=$k_1$ x pulse wave propagation time $$+\sum_i k_{2i} x$$

pulse wave analysis information $$+\sum_j k_{3j} x$$

body characteristic information +$k_4$ x body temperature,
where $k_1$, $K_{2i}$, $K_{3j}$ and $K_4$ define coefficient values respectively corresponding to the pulse wave propagation time, the pulse wave analysis information, the body characteristic information and the body temperature monitored from the regression analysis, which are predetermined values that are experimentally obtained; and
a display unit displaying the blood pressure calculated by the micro computer.

18. A blood pressure monitoring method comprising:
inputting body characteristic information of a subject;
monitoring an electrocardiogram signal of the subject;
emitting an optical signal of a predetermined frequency to the subject's body;
detecting an optical signal that has reflected from or penetrated the subject's body;
deemphasizing noise within the detected optical signal to generate a pulse wave signal;
calculating a pulse wave propagation time and a pulse wave analysis information using the monitored electrocardiogram signal and pulse wave signal; and
monitoring the blood pressure of the subject based on the calculated pulse wave propagation time, the pulse wave analysis information, and the body characteristic information, wherein monitoring the blood pressure includes inputting the pulse wave propagation time, the pulse wave analysis information and the body characteristic information in the following regression equation:
blood pressure (P)=$k_1$ x pulse wave propagation time $$+\sum_i k_{2i} x$$

pulse wave analysis information $$+\sum_j k_{3j} x$$

body characteristic information,
where $k_1$, $K_{2i}$, and $K_{3j}$ define coefficient values respectively corresponding to the pulse wave propagation time, the pulse wave analysis information, and the body characteristic information monitored from the regression analysis, which are predetermined values that are experimentally obtained.

19. The method as claimed in claim 18, wherein generating the pulse wave signal comprises:
generating an optical signal of a predetermined frequency and emitting the signal to the body of the subject;
receiving the optical signal that has penetrated or has been reflected from the body of the subject and converting the signal to an electric signal;
tuning the electric signal to a frequency band including the predetermined frequency to deemphasize the noise signal;
filtering the tuned electric signal to remove high frequency components; and generating the pulse wave signal based on the tuned and filtered electric signal.

20. The method as claimed in claim 18, wherein calculating the pulse wave analysis information comprises: calculating a pulse frequency of the subject; calculating a second derivative of the pulse wave signal; and calculating peak values of an acceleration waveform derived from the second derivative of the pulse wave signal.

21. The method as claimed in claim 18, wherein inputting the body characteristic information includes inputting at least one of sex, weight, height, length of an arm and age of the subject.

22. A blood pressure monitoring method comprising:
inputting body characteristic information of a subject;
monitoring an electrocardiogram signal of the subject;
emitting an optical signal of a predetermined frequency to the subject's body;
detecting an optical signal that has reflected from or penetrated the subject's body;
deemphasizing noise within the detected optical signal to generate a pulse wave signal;
monitoring a body temperature of a body part from which the pulse wave signal is monitored;
calculating a pulse wave propagation time and a pulse wave analysis information using the monitored electrocardiogram signal and pulse wave signal; and
monitoring the blood pressure of the subject based on the calculated pulse wave propagation time, the pulse wave analysis information the body characteristic information and the body temperature, wherein monitoring the blood pressure includes inputting the pulse wave propagation time, the pulse wave analysis information, the body characteristic information and the body temperature in the following regression equation:

blood pressure $(P) = k_1$ x pulse wave propagation time $$+ \sum_i k_{2i} x$$

pulse wave analysis information $$+ \sum_j k_{3j} x$$

body characteristic information $+k_4$ x body temperature, where $k_1$, $K_{2i}$, $K_{3j}$ and $K_4$ define coefficient values respectively corresponding to the pulse wave propagation time, the pulse wave analysis information, the body characteristic information and the body temperature monitored from the regression analysis, which are predetermined values that are experimentally obtained.

* * * * *